(12) United States Patent
Schreuder et al.

(10) Patent No.: US 8,468,625 B2
(45) Date of Patent: Jun. 25, 2013

(54) PATIENT GURNEY HAVING CONFIGURABLE REGISTRATION CAPABILITIES

(75) Inventors: Andries Nicolaas Schreuder, Bloomington, IN (US); John Leland Smith, Bloomington, IN (US); Bradley N. Keiser, Brazil, IN (US)

(73) Assignee: Procure Treatment Centers, Inc., New York, NY (US)

( * ) Notice: Subject to any disclaimer, the term of this patent is extended or adjusted under 35 U.S.C. 154(b) by 189 days.

(21) Appl. No.: 13/025,648

(22) Filed: Feb. 11, 2011

(65) Prior Publication Data

US 2011/0214235 A1  Sep. 8, 2011

Related U.S. Application Data

(60) Provisional application No. 61/304,395, filed on Feb. 12, 2010.

(51) Int. Cl.
*A47B 13/00* (2006.01)

(52) U.S. Cl.
USPC .................................................. 5/601; 5/611

(58) Field of Classification Search
USPC ..................................... 5/601, 611, 613, 614
See application file for complete search history.

(56) References Cited

U.S. PATENT DOCUMENTS

2011/0145991 A1 * 6/2011 Bridge et al. ..................... 5/601

FOREIGN PATENT DOCUMENTS

FR  EP0269528 A2 * 6/1987

* cited by examiner

*Primary Examiner* — Robert G Santos
*Assistant Examiner* — Brittany Wilson
(74) *Attorney, Agent, or Firm* — Shay Glenn LLP

(57) ABSTRACT

A patient support system includes a wheeled gurney having an upper support frame with at least one open side. A front support plate and a rear support plate are attached to the upper support frame, with the rear support plate spaced apart from the front support plate to correspond to the at least one open side. There is a first registration element positioned on the front support plate and a second registration element positioned on the rear support plate. The first and the second registration elements are repeatably moveable between a first registration configuration and a second registration configuration. A method of positioning a patient support on a gurney begins by identifying a registration feature on a surface of a patient support and then identifying a mating registration feature on wheeled patient gurney that corresponds to the registration feature. Next, there is a step of altering the configuration of the mating registration feature to permit the registration feature and the mating registration feature to engage when the patient support is placed on the wheeled patient gurney. The placing step is performed by a robot, for example. Alternatively, the placing step is performed in a radiation treatment room or performed while the patient support is supporting a patient undergoing a radiation therapy.

21 Claims, 10 Drawing Sheets

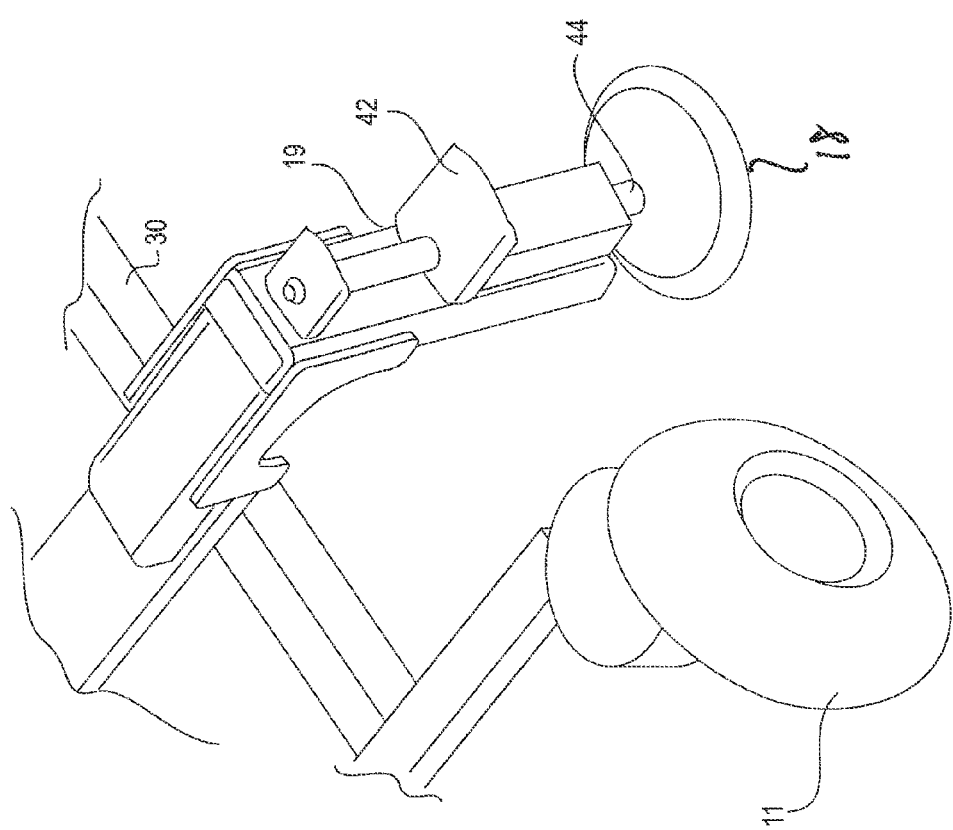

PATIENT GURNEY HAVING CONFIGURABLE REGISTRATION CAPABILITIES

CROSS REFERENCE TO RELATED APPLICATION

This application claims the benefit under 35 U.S.C. 119 of U.S. Provisional Patent Application No. 61/304,395, filed Feb. 12, 2010, titled "Patient Gurney Having Configurable Registration Capabilities", which is incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The present invention relates generally to patient support systems used in medical treatment systems, and especially in treatment systems utilizing robotic or mechanical means of positioning a patient.

BACKGROUND OF THE INVENTION

Patient transports or gurneys are used to simplify the task of moving patients within medical treatment centers. While these systems are useful for general mobility, there are treatments, especially when the patient is to be maneuvered during treatment by a robot or other controllable fixture, where more precise placement and registration of the patient and the patient support are needed. In the context of robotically assisted surgery, a patient support is often referred to as a robotic couch.

The use of robots for maneuvering and/or precisely positioning a patient are becoming increasingly wide spread as the use of robotic surgery systems increase. Robotic surgery systems offered, for example, by Intuitive Surgical (Sunnyvale, Calif.) as well as robotic radiosurgery systems offered, for example, by Accuray, Inc. (Sunnyvale, Calif.) are illustrative of the need within the field for precise placement of an immobilized patient. Millimeter and sub-millimeter accuracy requirements are required in certain circumstances. Some procedures, such as the application of therapeutic particle beams, now and in the future may require ever more accuracy in patient positioning.

As the development and use of robotic assisted treatment systems continues, it is likely that the need for every more precise patient positioning and registration of the immobilized patient relative to the robotic system will continue. In view of this progression in the field of robotically assisted surgery, there remains a need for improved patient transport systems suited for interaction with robotic systems. In addition, as robotic couches become more prevalent there is a need to provide a secure base for attachment to the gurney and consistent location to facilitate interaction with a robotic system.

SUMMARY OF THE INVENTION

In one aspect, a patient support system includes a wheeled gurney having an upper support frame with at least one open side; a front support plate and a rear support plate attached to the upper support frame, with the rear support plate spaced apart from the front support plate to correspond to the at least one open side; a first registration element positioned on the front support plate, a second registration element positioned on the rear support plate, wherein the first and the second registration elements are repeatably moveable between a first registration configuration and a second registration configuration. In one alternative, the first registration configuration and the second registration configuration are distinguished by the height of the registration element top surface to the top surface of the support plate coupled to the registration element. The patient support system has the rear support plate spaced apart from the front support plate sufficient to permit a robot arm to move between the rear support plate and the front support plate. In still other alternatives, there is a first hydraulic lift on the wheeled gurney connected to the front support plate and a second hydraulic lift on the wheeled gurney connected to the rear support plate. The first hydraulic lift moves the front support plate independent of how the second hydraulic lift moves the rear support plate, in some embodiments. In still other aspects of the patient support, the first and the second registration elements move between the first and the second registration configurations by rotating the registration element. The first and the second registration elements may move between the first and the second registration configurations by moving a portion of the registration element about a hinge connected to the support plate. In still other variations, the first and the second registration elements are connected by a hinge to the respective support plate. The patient support system may also include a registration pin attached to the wheeled gurney and moveable between an extended position and a retracted position and configured to engage with a floor mount when in the extended position.

In an additional embodiment there is a method of positioning a patient support on a gurney by identifying a registration feature on a surface of a patient support and then identifying a mating registration feature on wheeled patient gurney that corresponds to the registration feature. Next there is a step of altering the configuration of the mating registration feature to permit the registration feature and the mating registration feature to engage when the patient support is placed on the wheeled patient gurney. The method of positioning may also include placing a patient support on the wheeled gurney so as to engage the registration feature and the mating registration feature. The placing step is performed by a robot, for example. In one aspect, the placing step is performed in a radiation treatment room or performed while the patient support is supporting a patient undergoing a radiation therapy. In one variation, the registration feature is located on a surface of the patient support opposite of a surface on the patient support used to support a patient. In some embodiments, the patient support is a robotic couch.

In some aspects of positioning, the altering the configuration step will also include providing a perceptible indication on the mating registration feature of the type of patient support expected after performing the altering step. The perceptible indication is a word on the mating registration feature. The perceptible indication may be a color visible on a registration feature when it is configured to align with a corresponding color indicator on a robotic couch. In still another variation, the perceptible indication is a shape or orientation of the mating registration feature. In still another variation, the perceptible indication is a brand or trade name associated with a robotic couch adapted for use with a specific registration feature configuration on the gurney.

In another embodiment, there is a wheeled patient transport that has a wheeled gurney having an upper support frame with at least one open side; a front support plate attached to the upper support frame; a rear support plate attached to the upper support frame and spaced apart from the front support plate corresponding with the at least one open side; a registration element positioned on the top surface of the front support plate that is moveable between different registration orientations; and a registration element positioned on the top surface of the rear support plate that is moveable between different registration orientations. In another aspect of the wheeled patient transport the moveable registration element positioned on the top surface of the front support plate is connected to the front support plate by a hinge and the moveable registration element positioned on the top surface of the rear support plate is connect to the rear support plate by a hinge. In one alternative, the moveable registration element positioned on the top surface of the front support plate and the moveable registration element positioned on the top surface of the rear support plate each comprises a moveable aspect. In some configurations, the moveable aspect alters the height of a surface of the moveable registration element relative to a surface on the wheeled patient transport. In others, the moveable aspect alters the orientation of a moveable registration element relative to a surface on the wheeled patient transport.

In still another embodiment, there is a robotic couch support system that has a guide rail; a base coupled to and moveable relative to the guide rail; a lifting unit to move the base along the guide rail; an arm attached to and moveable along with the base; and a coupler on the arm. The robotic couch support system may also include a second guide rail adjacent to the guide rail and the base coupled to and moveable relative to the guide rail and the second guide rail. In one configuration, the lifting unit is attached to the base and moves along the guide rail with the base. In another variation, the lifting unit engages a feature on the guide rail to move the base along the guide rail. In another, the lifting unit uses a brake to hold the position of the base relative to the guide rail. The lifting unit is mounted in a fixed position relative to the guide rail, in some aspects. In other aspects, the lifting unit uses a motor to move the base along the guide rail. In still others, the lifting unit uses a hydraulic lift to move the base along the guide rail. The lifting unit may also be connected to the base with a cable. In an additional aspect, the coupler has at least one feature configured to engage with a feature on a robotic coupler used on a robotic couch. The feature used to engage may be any magnetic, electromechanical, mechanical or other suitable technique to releasably engage the coupler on the lifter with the coupler on the robotic couch just as is the practice when using patient positioning robots to couple with robotic couches.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 2 illustrates the gurney of FIG. 1 with a pin in position relative to an in-room registration monument;

DETAILED DESCRIPTION

Figure 1:
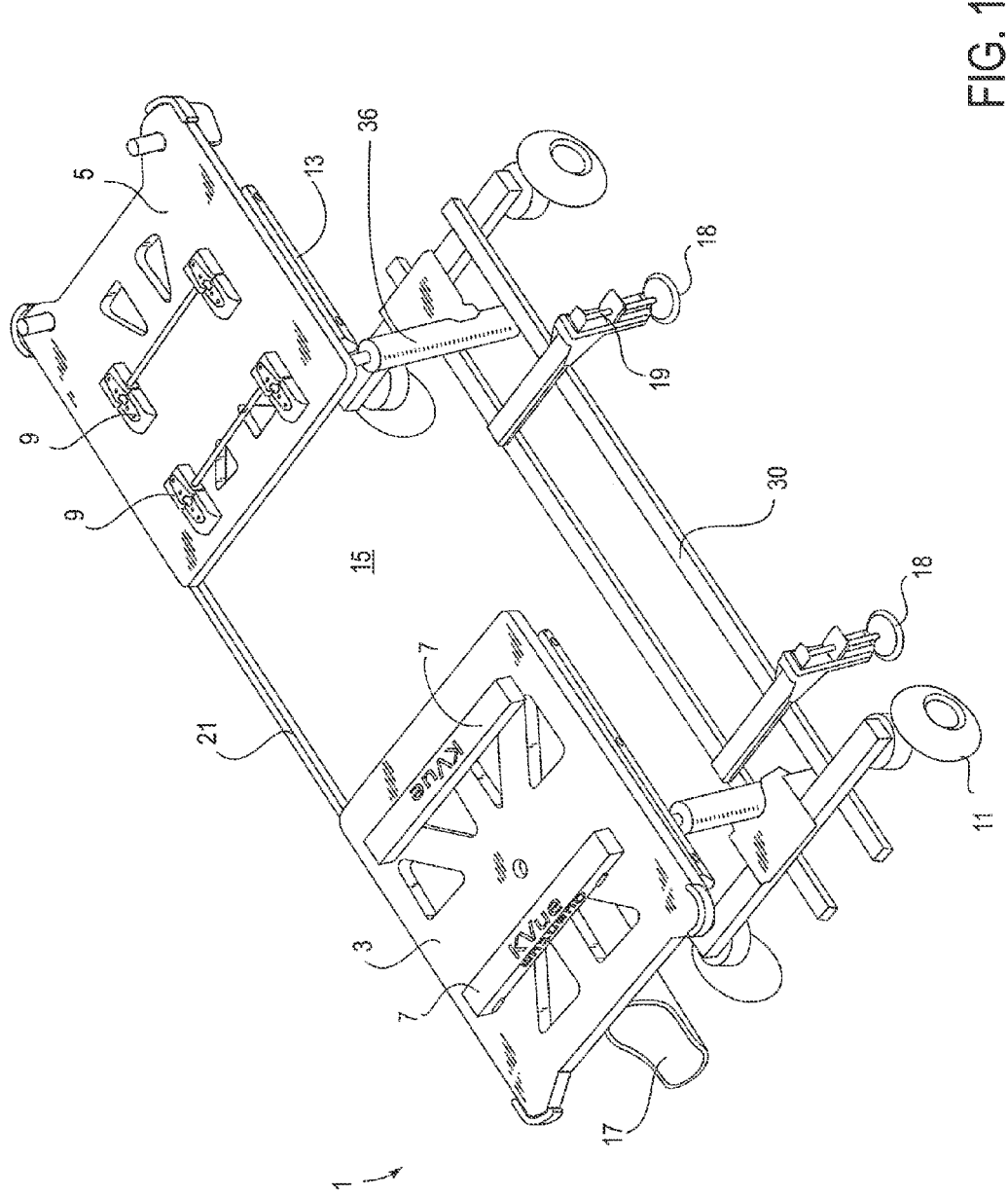
FIG. 1 is an isometric view of a gurney having configurable registration capabilities.

FIG. 1 is an isometric view of an exemplary patient support 1 having configurable couch registration capabilities. The patient support 1 includes a modified wheeled gurney base with an upper frame 21 conventionally attached to a lower wheel frame 30 either in a fixed position or in a movable position using an upper frame lifting system. The upper frame lifting system may include one or more hydraulic lifts (two lifts 36 are shown in FIG. 1) or other suitable lift system (e.g., electric motor, mechanical/manual like a crank or rack and pinion) used to permit the upper frame 21 to be raised, lowered, or locked into a position. Lifting systems are commonly used with a conventional patient gurney. The lower frame 30 supports the upper frame 21 as well as any provided upper frame lifting system along with wheels 11, casters or other device that enables mobility of the gurney.

In order to permit the patient support to be placed into and locked relative to a pre-determined treatment room floor position, the lower frame 30 also includes a registration element 19. The registration element is shown in relation above a floor mounted registration monument 38. The element 19 and monument are adapted and configured to engage using any suitable method. Exemplary engagements include magnetic, male/female couplers and the like.

The registration element 19 is shown is illustrated in a vertical orientation relative to the monument 38 but other orientations, such as lateral or horizontal, for example, as well as different types of registration elements, such as optical, electrical or electromechanical, for example, are possible depending upon the treatment room registration technique being used. Irrespective of the type of registration technique utilized, the registration element 19 position on the gurney—illustrated in FIG. 1 on the lower frame—is a precisely fixed and predetermined known or learned position for the robotic system used in a robotically assisted treatment room. The use of the registration element along with the treatment room registration element provides a registration between the patient support and the in-room robotic system or wall mounted lifter. Once positioned so that the registration elements engages with the monument, the robot then knows—either through programming, detection or other robotic registration technique, the position of the patient support 1, in particular, the upper frame opening 15.

FIG. 1 is an isometric view of a patient support 1 in position in a room having a pair of floor mounted registration monuments 18. There is a corresponding pair of registration elements 19 on the gurney lower frame 30. The registration elements 19 on the lower frame are positioned to align precisely with the pair of floor mounted registration monuments 18. FIG. 2 is a close up view of a registration element 19 above a floor mounted registration monument 18. The view in FIG. 2 illustrates the registration element pin 44 in a raised or unlocked position. The pin 44 is moved downward by pressing foot pedal 42 to extend pin 44 and seat it within the floor mounted registration element 18.

Returning now to FIG. 1, the upper frame 21 also supports the front support plate 3 and rear support plate 5. The front and rear support plates 3, 5 are attached to each end of the upper support frame 21 and spaced apart to form the opening 15. The opening 15 is a space provided to permit access to the underside of a robotic couch (not shown) that is supported by the front and rear support plates 3, 5. The opening 15 as well as the underside of the gurney in proximity to the opening 15 is sufficient to permit a robot to approach the underside of the robotic couch so that it may couple to or uncouple from the couch using a robotic coupling system. One exemplary robotic patient positioner and robotic coupler is described in commonly assigned U.S. patent application Ser. No. 12/208,807, filed Sep. 11, 2008, titled "Patient Positioner System," by Toby D. Henderson et al., the entirety of which is incorporated herein by reference.

At least one registration element is provided on either the front or the rear support plates. A registration element may be any feature that may be used to provide mating correspondence to a complementary element positioned on the lower surface or engaging surface of the robotic couch. A registration element may be fixed with respect to the top surface of a support plate. For example, a rectangular registration element may be fixed to the rear support plate top surface.

Additionally or alternatively, a fixed registration element—while remaining fixed at its base to the support plate—may have some other surface of the registration element removed or modified in order to place one or more registration features onto the fixed base. In one exemplary embodiment, the fixed base could be provided with sockets to receive specially shaped registration pins much like a socket driver may receive different sized or shaped sockets. Here, the fixed registration block on the support plate would be configured to receive different shaped registration pins. The registration pins may have a common base to connect to the openings in the fixed registration block on the support plate. The different shaped support pins could have any of a number of different shapes, features or structures to permit coupling to complementary features on the bottom of the robotic couch. In one alternative, a registration element may have one set of one or more sized, shaped or arranged sockets to engage with a robotic couch of a first type and then a second set of one or more sized, shaped or arranged sockets to engage with a robotic couch of a second type.

Additionally or alternatively, a registration element may couple to a support plate so as to change its registration characteristics or position by moving, such as by sliding or rotating, for example, relative to the support plate such as within or along the surface of a support plate.

Additionally or alternatively, a registration element may be moveable relative to the support plate. A registration element may move in any suitable way to change its orientation, size, shape or other characteristic in order to present another distinct registration characteristic. One exemplary moveable registration element is the registration element 9 shown in FIGS. 1, 3A and 3B. Additionally or alternatively, the registration block 7 shown on the support plate 3 in FIGS. 1, 4A and 4B may also be moveable relative to the support plate.

The embodiments of FIGS. 5A, 5B, 6A and 6B illustrate one type of registration element that changes its registration characteristic by rotating relative to the support plate 3. In both embodiments, a moveable support 135 is placed on, in or within the support plate in a first position to provide a first registration position.

Figure 5A:
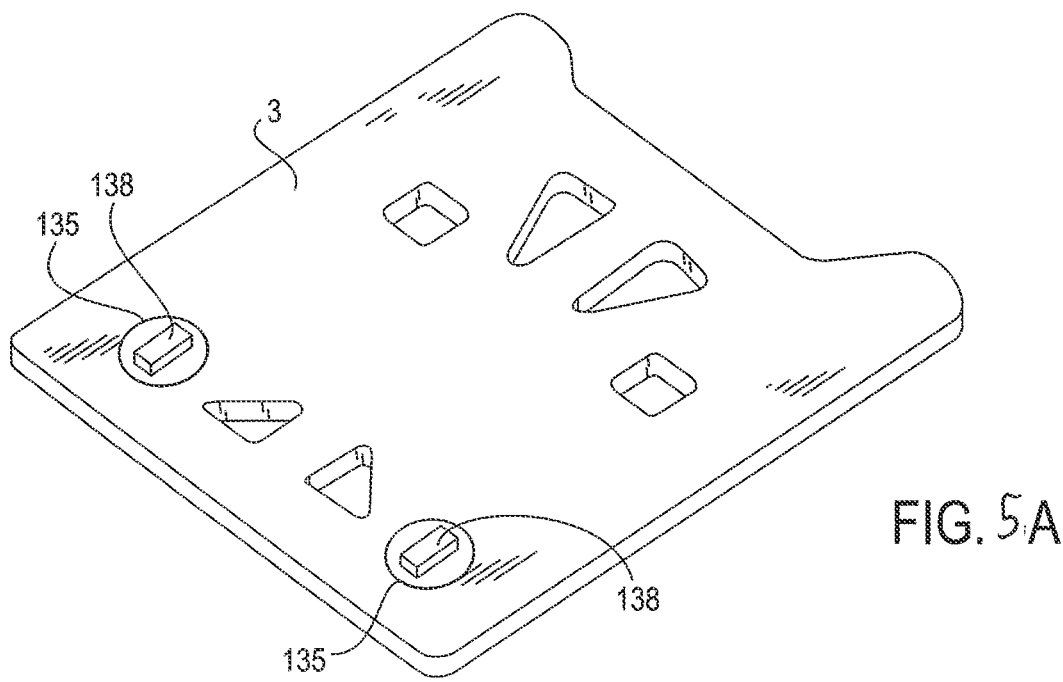
FIGS. 5A and 5B illustrate isometric views of a moveable registration element that is a raised rectangular feature on a support plate.
Figure 5B:
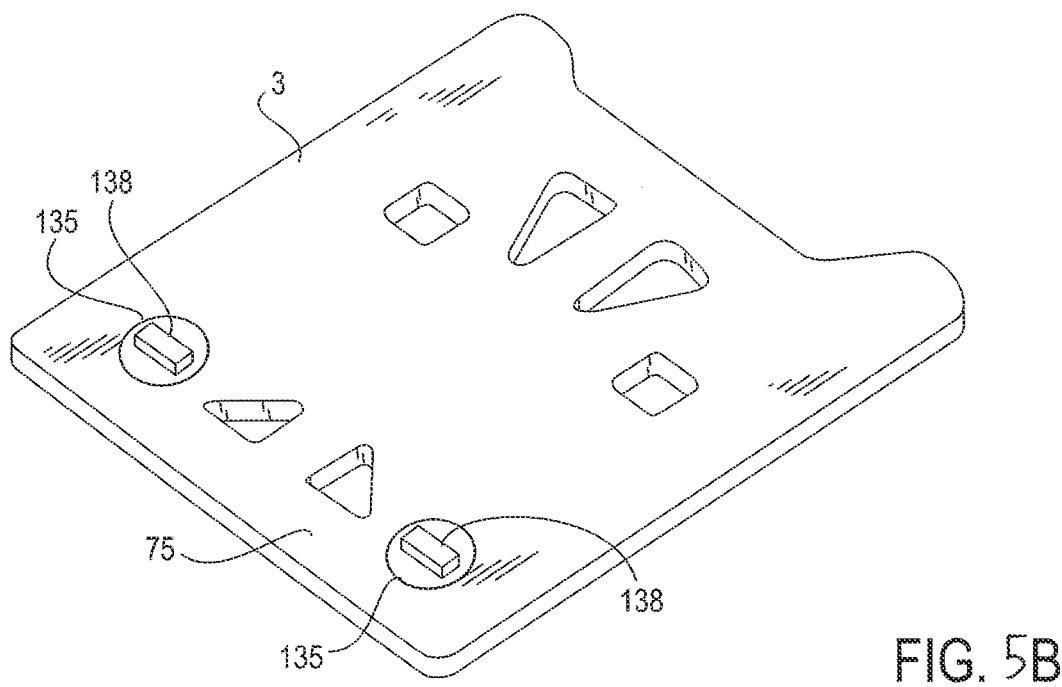

In the illustrative example of FIGS. 5A and 5B, the moveable support 135 has a registration element 138 on its upper surface. The registration element 138 is a raised rectangular structure. In FIG. 5A, the registration element 138 is shown having a first orientation of a registration characteristic. In contrast, FIG. 5B shows the position of the registration element 138 after moveable support 135 has been moved relative to the support plate about 90 degrees from the position shown in FIG. 5A. The registration element 138 in the configuration of FIG. 5B now presents a second, different registration characteristic to a robotic couch to be coupled to the patient support 1. A suitable robotic couch will include corresponding registration feature or features corresponding to the first or the second orientation of the element 138.

Figure 6A:
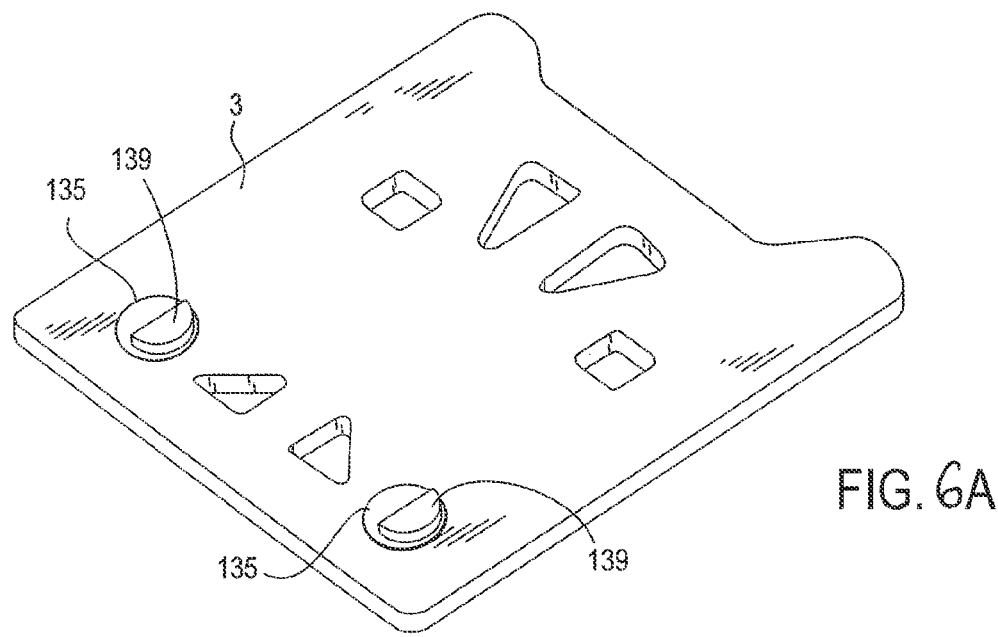
FIGS. 6A and 6B illustrate isometric views of a moveable registration element that is a raised crescent or semicircle feature on a support plate.
Figure 6B:
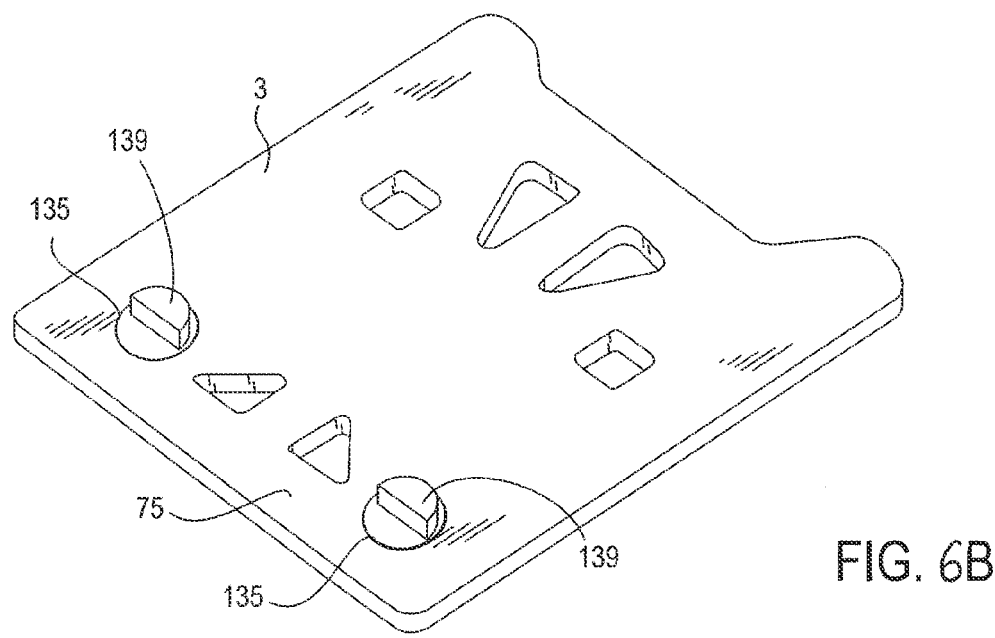

FIGS. 6A and 6B illustrate another embodiment of the moveable support 135 that has a raised crescent shaped registration element 139. FIGS. 6A and 6B show the movement of the support 135 to present the crescent registration figure in two different registration positions having distinct registration characteristics and orientation for coupling with corresponding registration elements on a robotic couch.

In other additional and alternative embodiments of those shown in FIGS. 5A-6B, different registration elements may be positioned on the moveable support. In addition, the moveable support may move in steps larger or smaller than the ones illustrated. Additionally or alternatively another registration or indexing device or system may be used between the moveable support 135 and the support plate. For example, the support plate 135 may be positioned in a recess of the support plate 3, 5 that includes gearing or a ratchet to ensure the support 135 is positioned relative to the support plate 3, 5 in the proper or desired orientation. Features, indications or marking on, in or coupled to one or both of the moveable support 135 and/or the respective support plate 3, 5 may also be used to ensure that the desired engagement characteristic is presented. The example of a rotating registration element 135 is provided on the support plate 3 for purposes of illustration only. It is to be appreciated that any of the registration elements described herein may be used with either or both support plates 3, 5 in any combination.

Figure 3A:
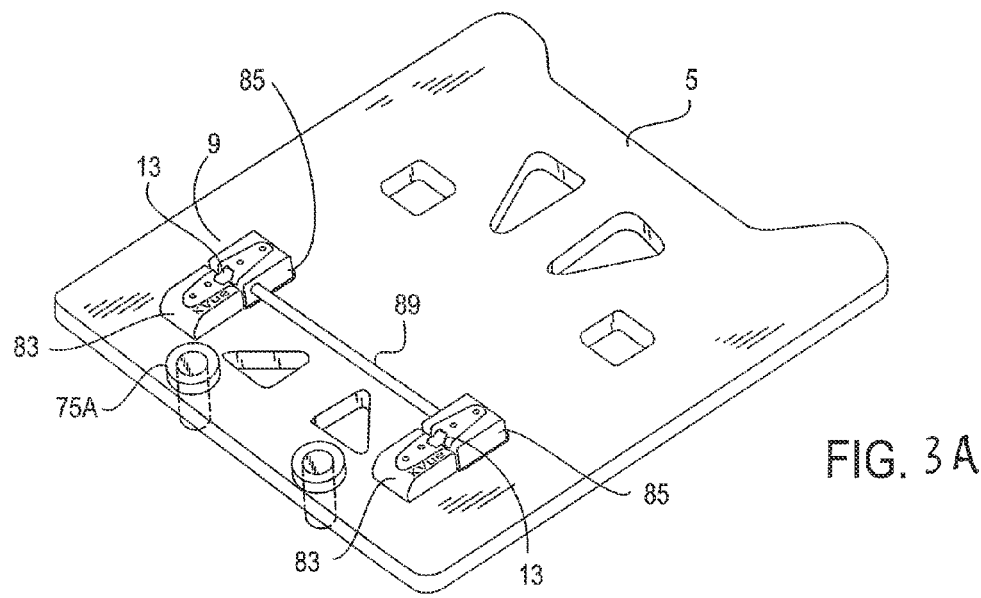
FIGS. 3A and 3B illustrate isometric views of a registration feature that is hinged to move relative to a support plate.
Figure 3B:
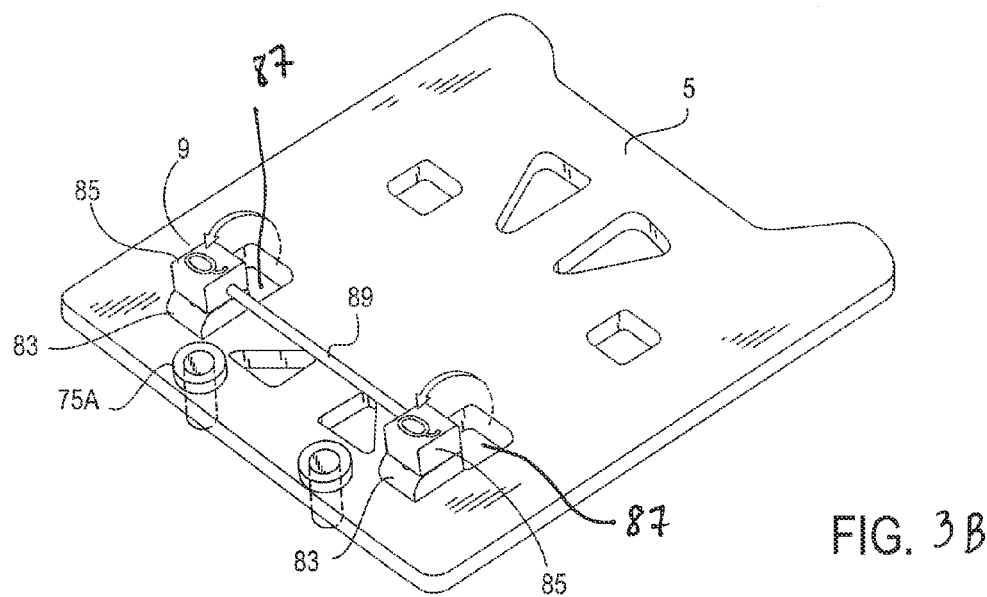

FIGS. 3A and 3B illustrate isometric views of one embodiment of a moveable registration element on the support plate 5. The moveable registration element in this embodiment includes a pair of lower blocks 83 attached to the support plate 5. In the illustrated embodiment, a pair of upper blocks 85 are attached to the lower blocks 83 by hinges 13 as well as a cross bar 89. Linking the upper blocks 85 by a cross bar 89 allows both of the upper blocks 85 to move together in a single motion as shown in FIG. 3B.

As the upper blocks 85 are moved, they move from a first registration configuration or position (FIG. 3A) and come to rest in a second registration position (FIG. 3B). As shown in FIG. 3B, an appropriately sized recess 87 is formed in the support plate to receive the top blocks 85.

Another aspect of registration, present in some registration embodiments described herein, is the use of marks, symbols, identification elements or other indicia to provide a visual que to a user of the type, model, brand or other identifier of robotic couch type best suited to the current registration scheme or configuration. Refer, for example, to the configurations of FIGS. 3A-4B. The registration configuration visible in FIGS. 3A and 4A bears a marking "KVue." This configuration would indicate to a user that the gurney is in a registration configuration to accept a "KVue" style robotic couch. This indicates to a user that when the blocks are so configured, the support plate has registration characteristics to pair with a "KVue" style couch having corresponding registration elements attached thereto. In contrast, the registration configuration in of FIGS. 3B and 4B bears a marking "Q" and Quantum, respectively. This registration configuration would indicate to a user that the gurney is in a registration configuration to accept a "Q" style or Quantum robotic couch having corresponding registration elements attached thereto. This indicates to a user that when the blocks are so configured, the support plate has registration characteristics to pair with a "Q" style couch. The names of the couch style here are used only of purposes of example. Any identifying mark may be used such as names, nicknames, logos, slogans, colors or other indicia, to permit a user with a quick visual scan to identify the registration characteristic of a gurney. Indications of registration configuration are also found in FIGS. 5A-6B.

Figure 4A:
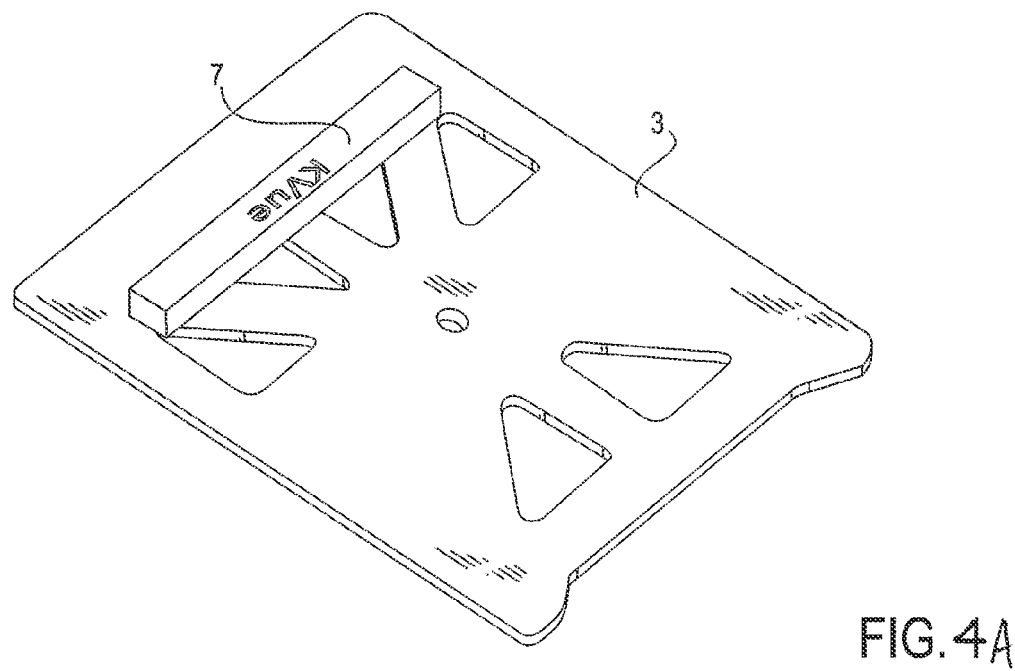
FIGS. 4A and 4B illustrate isometric views of a registration feature that is hinged to move relative to a support plate.
Figure 4B:
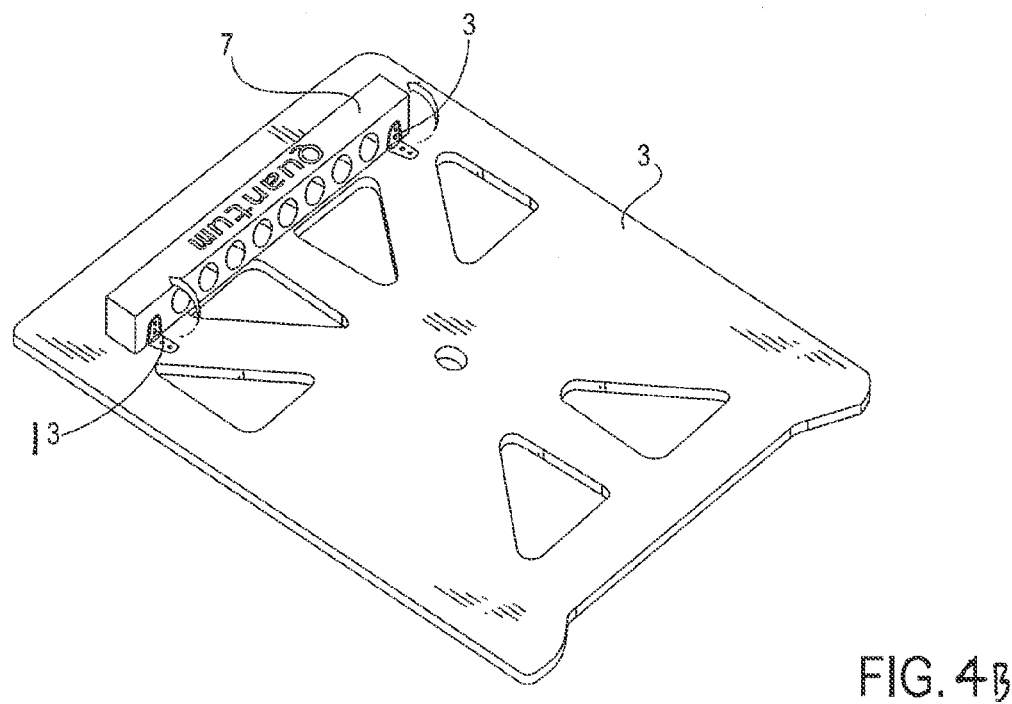

FIGS. 4A and 4B illustrate an isometric view of one embodiment of a registration element on the support plate 3. In contrast to the separately positioned registration element shown in FIGS. 3A and 3B the registration element 7 on the support 3 may hinged directly to the support plate 3. Like the other hinged registration embodiments, the registration element in these figures is also configured for hinged movement relative to a support plate. FIG. 4A illustrates the registration element 7 in a "down," hinge closed or first registration position. In this registration position, the registration element bottom is against the support plate top surface. FIG. 4B is a top down isometric view of the registration element 7 in an up or hinge open position. In this second registration position, the bottom surface of the registration element is rotated by the hinge 13 to be separated from the support plate surface. In contrast to the hinged embodiment above where the support plate 5 surface was recessed 87 to permit block 85 movement, in this hinged registration element configuration, the configuration element 7, not the support 3, is recessed to accommodate the hinge 13.

A registration pin may also extend from the bottom of a robotic couch. In one example, the pin is configured to engage directly with the opening in a support plate or using a registration sleeve 75A shown in FIGS. 3A and 3B. A suitable robotic couch may be modified to include any appropriate complementary registration feature of any support plate, registration feature, registration orientation, registration mode or registration technique described herein.

Irrespective of the type of registration element used, the registration element or elements are provided to ensure the desired alignment between a robotic couch to be supported by the gurney and the gurney. A robotic couch appropriately coupled to a gurney registration element will place a robotic couch coupler on the couch within the gurney opening 15. Importantly, engagement between a support plate registration element and the robotic couch ensures that the robotic couch is reliably and precisely placed relative to the gurney opening. The cooperative registration between the support plate to the robotic couch and the frame registration to the room registration monument ensures that the robotic coupling on the robotic couch is now in a position to be accessed by or determined by a robotic system.

Figure 7:
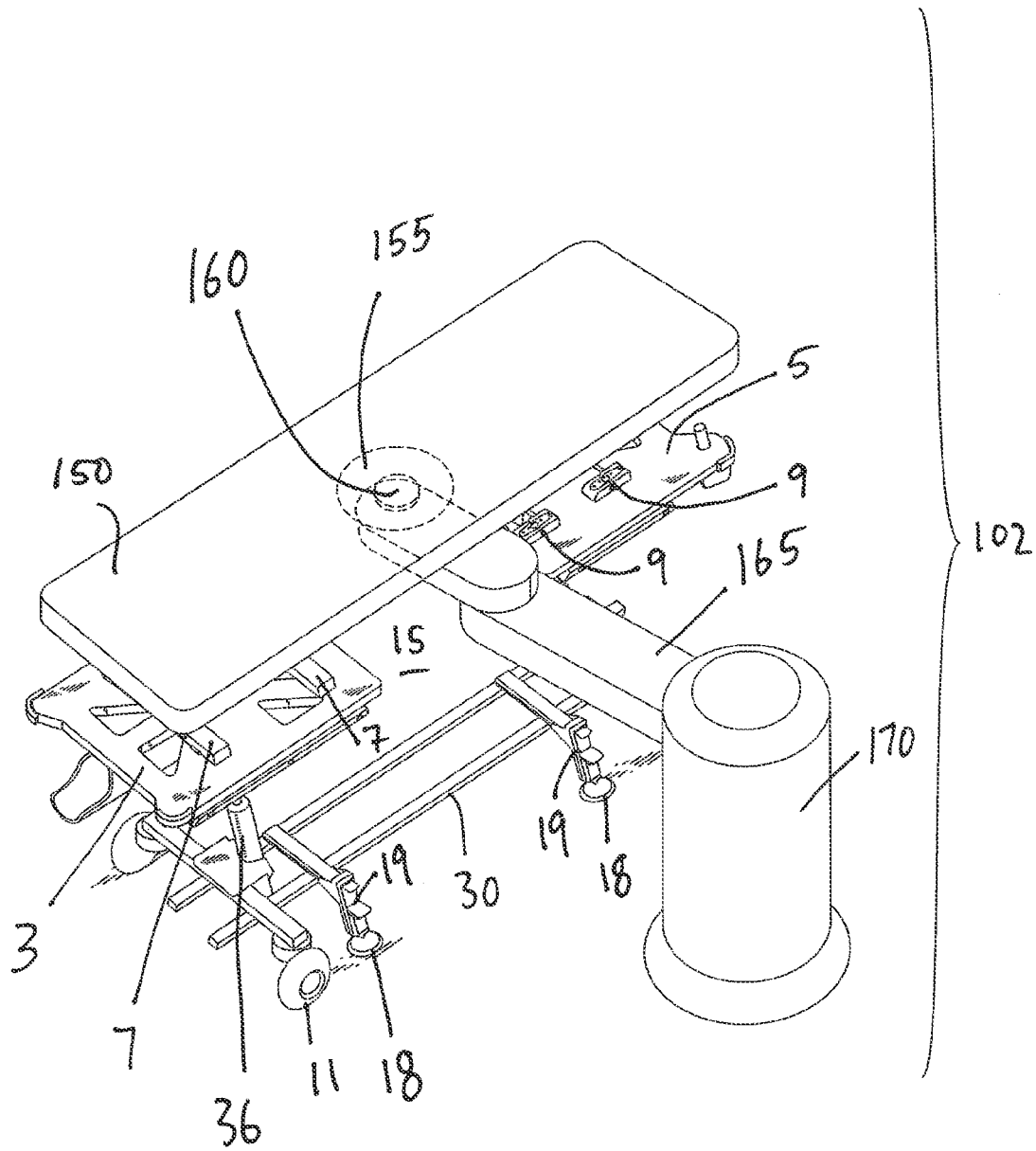
FIG. 7 is an isometric view of an in room robotic positioned reaching into the opening 15 in a gurney to engage with and lift a robotic couch.

FIG. 7 is an isometric view of a robotic positioning system coupled to and lifting a robotic couch. This figure also illustrates how a robotic positioning system (represented here by a robotic base 170, 2 part arm 165, and coupler 160) can maneuver into opening 15, engage with couch coupler 155 and lift couch 150 clear of gurney and into position for treatment.

In addition, registration elements and/or support plates may also be designed or configured to support many different types of robot couches, includes couches that may support additional equipment for patient restraints, supports or monitoring equipment. One example of a robotic couch that also provides on board anesthesia capabilities is described in U.S. Provisional Patent Application Ser. No. 61/304,278, filed Feb. 12, 2010, titled "Robotic Mobile Anesthesia System," by Niek Schreuder and U.S. patent application Ser. No. 13/025, 529 filed Feb. 11, 2011, titled "Robotic Mobile Anesthesia System", by Andries Nicolaas Schreuder, the entirety of which are incorporated herein by reference. Accordingly, registration elements and/or support plates may be provided to support such a couch as described in the above applications.

Through the use of complementary registration elements or features on a support plate and the robotic couch, a wide variety of unique registration element combinations may be created. Through the use of unique registration elements, a single gurney may be used to ensure the precise placement of a wide variety of different robotic couches. Robotic couches may vary depending upon a number of factors such as the manufacturer or specific purpose of the robotic couch. A robotic couch may be manufactured with or equipped with a specific registration feature or a registration feature may be attached (i.e., a user may purchase a robotic couch and then install one or more specific registration features from a kit) in order to facilitate coupling to the support plate registration feature.

Figure 8:
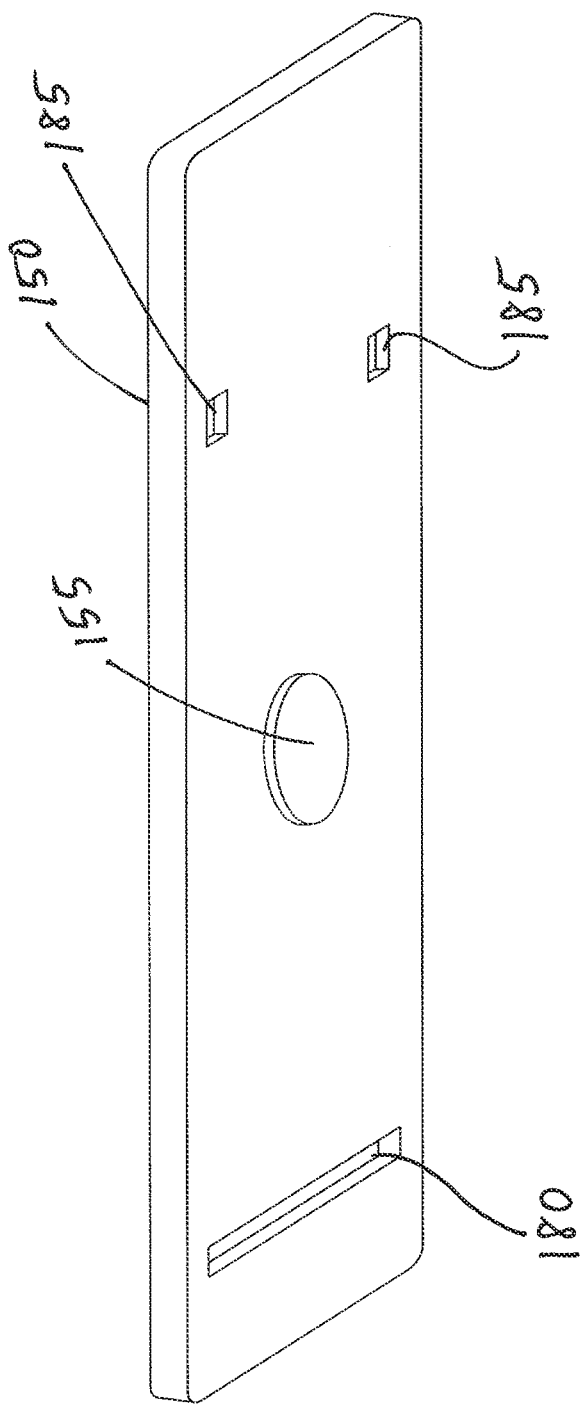
FIG. 8 is a bottom up view of the underside (i.e., the side that engages with a robotic coupler) of a robotic couch having recesses formed and positioned to correspond to a configurable gurney registration feature.

Registration characteristics may also be developed based upon the height, area or volume of a registration feature. Consider first the registration configuration of FIG. 3A. Prior to the movement of the moving block, the block has a first height (h1) and a first area (A1) on the surface of the plate 5. This is an example of a first registration position. In FIG. 3B, upon block movement, the block now has a second height (h2) and a second area (A2) on the surface on the support plate 5. This is an example of a second registration position. The differences in appearance namely h1 is less than h2 and area A1 or footprint is larger than area A2 may be easily identified by a user to note the specific registration configuration in use. Moreover, it is to be appreciated that the distribution of the volume of the registration element above the support plate is also different in these illustrative registration positions. As such, registration characteristics may vary by any of a number of features such as height, area, volume, orientation and/or shape. Differences in registration characteristics will produce corresponding registration features on robotic couches modified to work with the patient gurney described herein. FIG. 8 is a bottom up view of a robotic couch 150 modified to correspond to the registration configuration of FIGS. 4B and 3B. A recess 180 is provided that corresponds to registration feature 7 in FIG. 4B. Similarly, a pair of recesses 185 is also provided to correspond to feature 9 in FIG. 3B.

Figure 9:
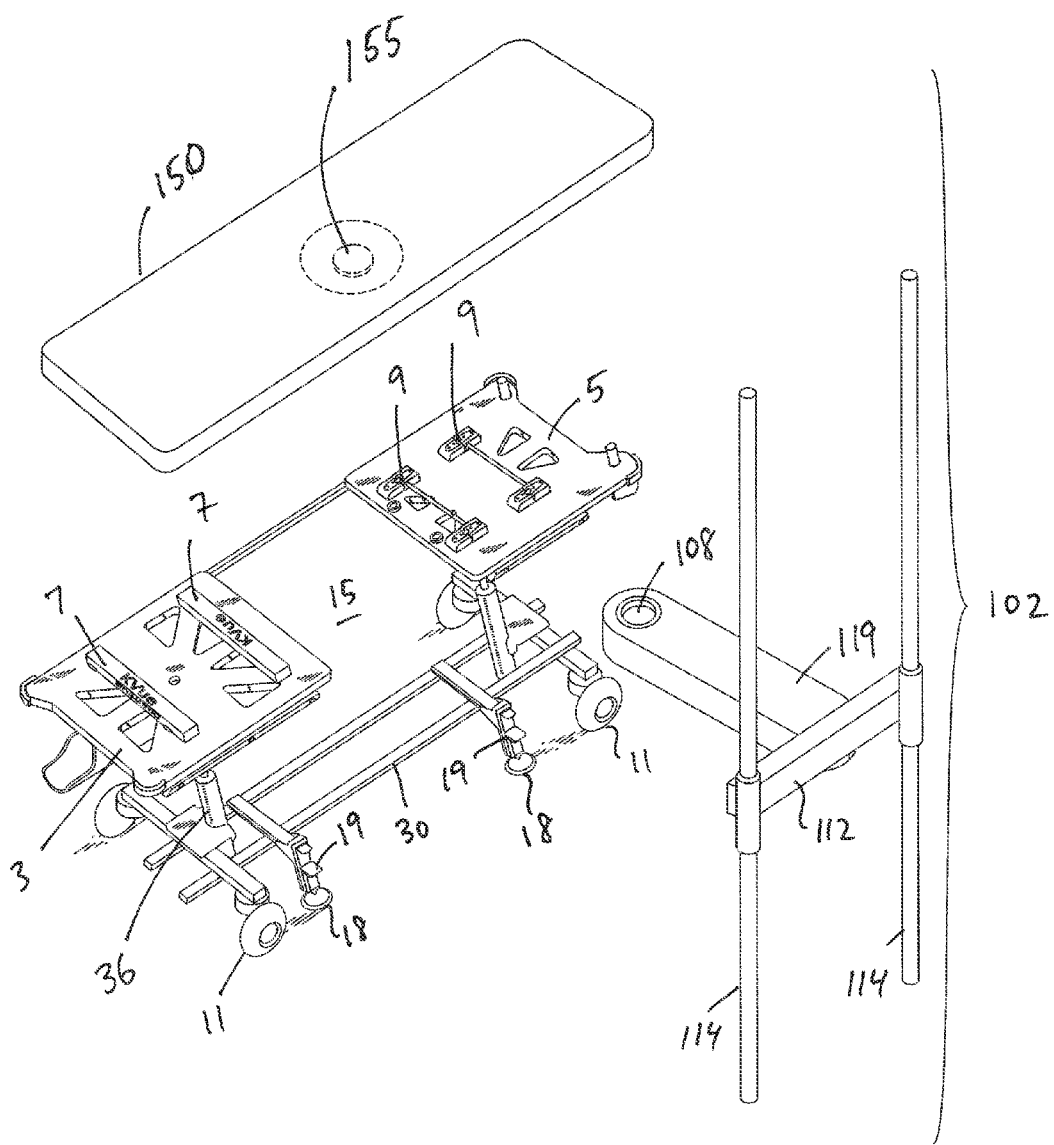
FIGS. 9 and 10 illustrate an exploded and in use view, respectively, of an embodiment of a stand alone couch system with a lifting unit capable of positioned below and coupling to a robotic couch including being engaged so as to lift the couch above the gurney as shown in FIG. 10.
Figure 10:
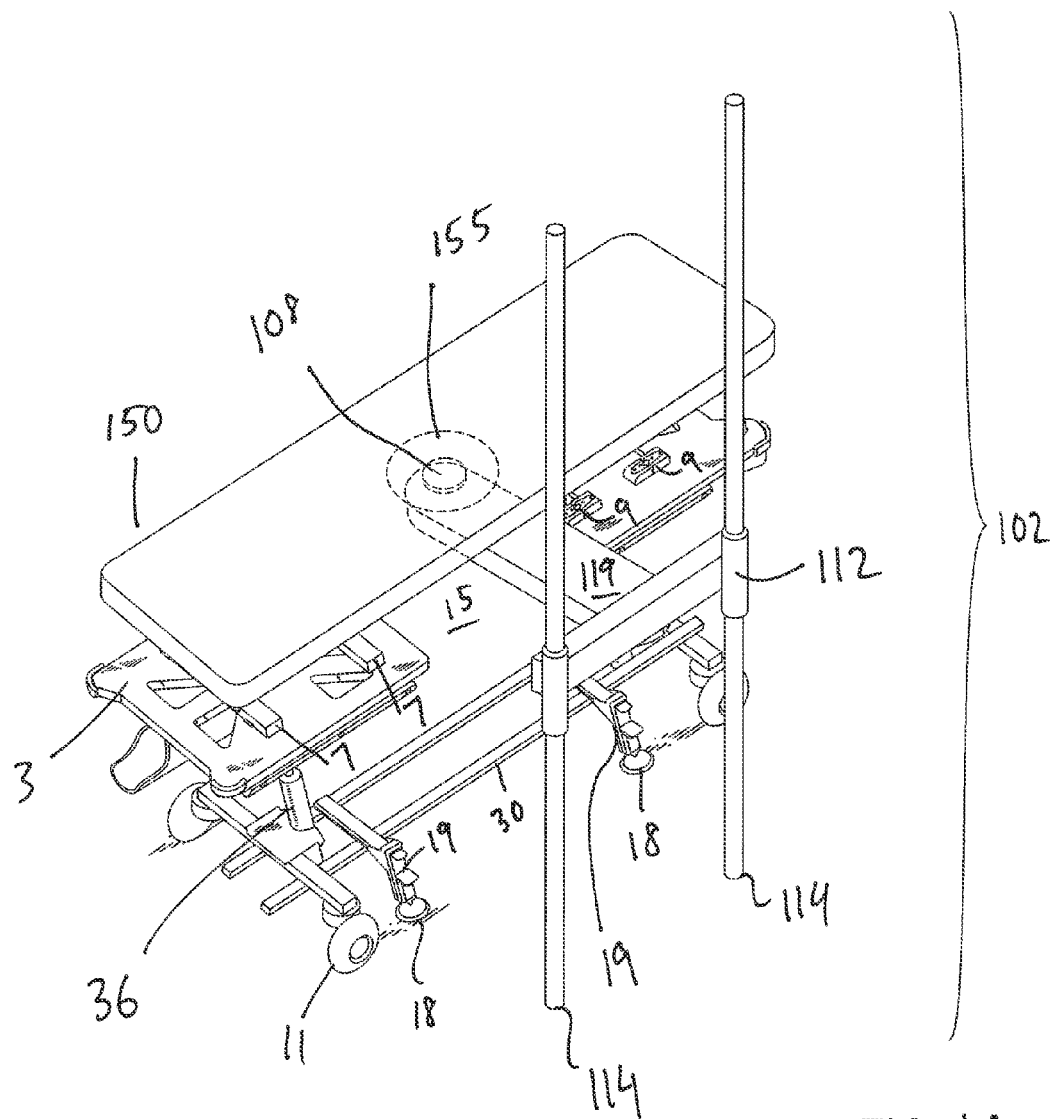

FIGS. 9 and 10 illustrate one embodiment of a stand alone couch support system 102. The system 102 is shown in an exploded configuration (FIG. 9) and in use lifting a robotic couch 150 from a gurney (FIG. 10). This embodiment illustrates a wall based docketing station configured to, like the patient positioning robot (FIG. 5), move an appropriate couch coupler 108 into the opening 15 to engage with the coupler or receiver 155 positioned on the bottom or presented aspect of a robotic couch 150. The coupler 108 is positioned on a lifting unit 112 that is supported by one or a pair guide rails 114. The guide rails 114 are secured to a wall or other suitable support that provides a stable base of support for the combined weight of the lifting unit, couch coupler 108, arm 119, robotic couch 150 and a patient. Additionally, the guide rails are appropriately supported based on the type of lifting unit used in the system. The source to provide lifting power may be contained within the lifting unit 112. Additionally or alternatively, the lifting unit 112 may be placed on each guide rail 114 at the top or bottom and configured as a direct drive unit. In another alternative, the coupler 108 and arm 119 may be moved to engage with the robotic couch 150 using a hydraulic system similar to an elevator. In another alternative, the coupler 108 may be moved to engage with the robotic couch using a chain or belt driven system, a rack and pinion driven system, a magnetic drive system or any other type of system that can controllably direct the movement of the coupler 108 and arm 119. The lifting unit 112 may simply be a base used to join arm 119/coupler 108 in moving relation to one rail 114 or a pair of rails 114.

In use, the coupler 108 is initially in a lowered position that is any position beneath the lowest point of the robotic couch to be engaged. This first position permits the movement of the gurney bearing a patient on a robotic couch into position suited to engagement of the coupler by activation of the drive system. Gurney registration with the lift system 102 may be done with or without registration to a floor monument.

Next, the lift system is activated to move up into contact with and engage the coupler on the robotic couch. If desired, coupling between the couch and the lifting system may be confirmed. Thereafter, the drive system is engaged to raise the robotic couch and lift the couch clear of the gurney support plates. Importantly, the drive system has sufficient vertical drive range to clear the support plates and completely disengage any registration features used to align the robotic couch with the gurney.

Once the patient is supported by the wall support unit, the lifting unit may be controlled to position the patient at any elevation within the drive limits of the system. Some patients my prefer a lower position such as that found in a chair or sofa. Once the patient and couch are offloaded onto the wall drive system, the gurney may now be used to transport another patient to another robotic assisted medical procedure. When the patient is ready to leave, the lift system is operated to adjust the height of the robotic couch to allow the patient to get off of the couch. The lift system may then be operated to return the coupler to a "ready to dock" position where it is ready to engage with another gurney/robotic couch.

In one additional alternative of FIGS. 9 and 10, the wall mounted coupler 108 is designed to have the operational capabilities if the coupler illustrated and described with regard to FIGS. 1 and 6 in U.S. patent application Ser. No. 12/208,807 mentioned above.

A pad (not illustrated) is also provided that converts the gurney to one where a patient may lay directly on it. The pad has a length and width selected to cover the front and rear support plates 3, 5 and the opening 15. The pad has a top surface that is padded for patient comfort and support. The underside of the pad is appropriately hollowed or recessed to fit over or around any registration features on or coupled to the support plates, similar to recesses 180, 185 in couch 150 (see FIG. 8).

While preferred embodiments of the present invention have been shown and described herein, it will be obvious to those skilled in the art that such embodiments are provided by way of example only. Numerous variations, changes, and substitutions will now occur to those skilled in the art without departing from the invention.

By way of example, in addition to mechanical registration (i.e., mating of complementary parts) described herein, registration as used in this application may also be the use of any suitable form of coupling such as electromechanical, electrical, optical, magnetic or other available coupling or interlock system. Moreover, it is to be appreciated that the registration elements may represent hybrids registration elements that combine one or more of the registration techniques described herein.

Hybrid registration elements may include mechanical registration augmented by another type of registration such as bar code reader/scanner, RFD or other electronic tagging, electrical reed switches, photo cells, light beams or optical or other suitable sensors to confirm, indicate or identify not only proper registration and/or engagement between the support plate and robotic couch registration elements but to also confirm that the positioned robotic couch on the gurney is the robotic couch type expected or desired by the robotic system. As such, registration techniques described herein also permit a robotic system to interrogate using any suitable means (i.e., optical, bar code scanning, RFD, or other suitable electrical, mechanical or magnetic interrogation technology) a robotic couch prior to coupling in order to determine or confirm that the proper or expected couch/patient is about to be engaged by the robot.

It should be understood that various alternatives to the embodiments of the invention described herein may be employed in practicing the invention.

What is claimed is:

1. A patient support system comprising:
   a wheeled gurney having an upper support frame with at least one open side;
   a front support plate and a rear support plate attached to the upper support frame, with the rear support plate spaced apart from the front support plate sufficient to permit a robot arm to move between the rear support plate and the front support plate and corresponding to the at least one open side; and
   a first registration element positioned on the front support plate, a second registration element positioned on the rear support plate, wherein the first and the second registration elements are repeatably moveable between a first registration configuration and a second registration configuration.

2. The patient support system of claim 1 wherein the first registration configuration and the second registration configuration are distinguished by the height of the registration element top surface to the top surface of the support plate coupled to the registration element.

3. The patient support system of claim 1 further comprising: a first hydraulic lift on the wheeled gurney connected to the front support plate and a second hydraulic lift on the wheeled gurney connected to the rear support plate.

4. The patient support system of claim 3 wherein the first hydraulic lift moves the front support plate independent of how the second hydraulic lift moves the rear support plate.

5. The patient support system of claim 1 wherein the first and the second registration elements move between the first and the second registration configurations by rotating the registration element.

6. The patient support system of claim 1 wherein the first and the second registration elements move between the first and the second registration configurations by moving a portion of the registration element about a hinge connected to the support plate.

7. The patient support system of claim 1 wherein the first and the second registration elements are connected by a hinge to the respective support plate.

8. The patient support system of claim 1 further comprising: a registration pin attached to the wheeled gurney and moveable between an extended position and a retracted position and configured to engage with a floor mount when in the extended position.

9. A method of positioning a patient support on a gurney, comprising:
   identifying a registration feature on a surface of a patient support, the patient support comprising a robotic couch;
   identifying a mating registration feature on wheeled patient gurney that corresponds to the registration feature;
   altering the configuration of the mating registration feature to permit the registration feature and the mating registration feature to engage when the patient support is placed on the wheeled patient gurney.

10. The method of positioning a patient support according to claim 9 further comprising: placing a patient support on the wheeled gurney so as to engage the registration feature and the mating registration feature.

11. The method of positioning a patient support according to claim 10 wherein the placing step is performed by a robot.

12. The method of positioning a patient support according to claim 10 wherein the placing step is performed in a radiation treatment room.

13. The method of positioning a patient support according to claim 10 wherein the placing step is performed while the patient support is supporting a patient undergoing a radiation therapy.

14. The method of positioning a patient support according to claim 9 wherein the registration feature is located on a surface of the patient support opposite of a surface on the patient support used to support a patient.

15. The method of positioning a patient support according to claim 9 the altering the configuration step further comprising: providing a perceptible indication on the mating registration feature of the type of patient support expected after performing the altering step.

16. The method of positioning a patient support according to claim 15 wherein the perceptible indication is a word on the mating registration feature.

17. The method of positioning a patient support according to claim 15 wherein the perceptible indication is a shape or orientation of the mating registration feature.

18. A wheeled patient transport, comprising:
   a wheeled gurney having an upper support frame with at least one open side;
   a front support plate attached to the upper support frame;
   a rear support plate attached to the upper support frame and spaced apart from the front support plate corresponding with the at least one open side;
   a registration element positioned on the top surface of the front support plate that is moveable between different registration orientations and is connected to the front support plate by a hinge; and
   a registration element positioned on the top surface of the rear support plate that is moveable between different registration orientations and is connected to the rear support plate by a hinge.

19. The wheeled patient transport of claim 18 wherein the moveable registration element positioned on the top surface of the front support plate and the moveable registration element positioned on the top surface of the rear support plate each comprises a moveable aspect.

20. The wheeled patient transport of claim 19 wherein the moveable aspect alters the height of a surface of the moveable registration element relative to a surface on the wheeled patient transport.

21. The wheeled patient transport of claim 19 wherein the moveable aspect alters the orientation of a moveable registration element relative to a surface on the wheeled patient transport.

* * * * *